United States Patent [19]

Hotta et al.

[11] 4,028,331

[45] June 7, 1977

[54] ULTRA VIOLET ABSORBER

[75] Inventors: Seiji Hotta, Ibaraki; Koichi Koga, Oita; Tomoyuki Bando, Ibaraki; Yutaka Kondo, Tokyo, all of Japan

[73] Assignees: Sumitomo Chemical Company, Limited; Kyodo Chemical Company, Ltd., both of Japan

[22] Filed: Feb. 4, 1975

[21] Appl. No.: 547,091

[30] Foreign Application Priority Data

Feb. 8, 1974  Japan ............................ 49-16435

[52] U.S. Cl. ..................... 260/45.8 NT; 252/401; 252/402; 252/403; 252/404; 260/45.8 N; 260/45.8 NW; 260/45.8 SN; 260/45.85 B; 260/45.95 E; 260/45.95 C; 260/45.95 H

[51] Int. Cl.² .................... C08K 5/13; C08K 5/34; C08K 5/46

[58] Field of Search ............ 260/45.8 NT, 45.8 SN, 260/45.9 R

[56] References Cited

UNITED STATES PATENTS

| | | | |
|---|---|---|---|
| 3,004,896 | 10/1961 | Heller et al. ...................... 260/45.8 |
| 3,072,585 | 1/1963 | Milionis et al. ....................... 260/22 |
| 3,239,483 | 3/1966 | Higgins ............................ 260/45.8 |
| 3,244,667 | 4/1966 | Burgess .......................... 260/45.75 |
| 3,300,445 | 1/1967 | Sidi ...................................... 260/67 |
| 3,326,849 | 6/1967 | Kelly, Jr. et al. ................. 260/45.8 |
| 3,368,997 | 2/1968 | Gordon ............................ 260/45.8 |
| 3,379,675 | 4/1968 | Jensen et al. ..................... 260/45.8 |
| 3,538,046 | 11/1970 | Oertel et al. ..................... 260/45.9 |
| 3,640,928 | 2/1972 | Murayama et al. ................. 260/23 |
| 3,642,669 | 2/1972 | Nast et al. .......................... 260/2.5 |
| 3,778,409 | 12/1973 | Oertel et al. ..................... 260/45.8 |
| 3,856,749 | 12/1974 | Hoeschele ....................... 260/45.9 |

*Primary Examiner*—Lewis T. Jacobs
*Assistant Examiner*—R. A. White
*Attorney, Agent, or Firm*—Wenderoth, Lind & Ponack

[57] ABSTRACT

A ultraviolet of absorber containing 2-(2',4'-dihydroxyphenyl)-5-chlorobenzotriazole is effectively used to stabilize polyurethane resins against ultraviolet rays.

9 Claims, 2 Drawing Figures

ULTRA VIOLET ABSORBER

The present invention relates to a ultraviolet absorber for polyurethane resins. High molecular weight polyurethane resins which are prepared from polyhydroxyl compounds, chain-propagator and chain-propagator are widely used in the form of foam, elastomer, film, foil or elastomer yarn. However, they are unstable upon exposure to sunlight and in some cases to hot air. This instability, which is due to the structural characteristics of the resins to some extent, brings about a reduction in the mechanical strength and in most cases a great deal of discoloration. In order to protect the resins from reduction and discoloration, many attempts have been made to incorporate well-known antioxidants and ultraviolet absorbers into the resins, but the results have not generally been satisfactory.

Many v.-triazoles, particularly benzotriazole compounds, have been known as ultraviolet absorber and some of them are commercially available. But practically, the results are not always satisfactory, because most of the v.-triazoles have a low ultraviolet ray-absorbing power, poor light fastness, an inevitable color which is responsible for coloring or staining the materials to be protected, poor thermal stability, a high sublimability, or further, low compatibility with or affinity for organic substances.

Japanese Patent Publication Nos. 2476/1962, 7863/1963 and 4768/1967 disclose ultraviolet absorbers comprising v.-triazole compounds which are, however, still unsatisfactory for protecting polyurethane resins from the above mentioned adverse influences of ultraviolet ray. In general, ultraviolet absorbers usable in practice for polyurethane resins should have the following properties:

1. excellent protective effects against degraddation of polyurethane resins due to ultraviolet rays,
1. low sublimation by heat,
3. good compatibility with polyurethane resins to be incorporated thereinto,
4. no coloration on incorporating into polyurethane resins, and
5. facility of purification to permit obtention in a pure form.

The present inventors have conducted studies to find a ultraviolet absorber which can be used in practice for protecting polyurethane resins from the above mentioned adverse influences of ultraviolet ray, and found that 2-(2',4'-dihydroxyphenyl)-5-chlorobenzotriazole is effective for use in the ultraviolet absorber.

Thus, the present invention provides a ultraviolet absorber for preparing a stable polyurethane resin comprising 2-(2',4'-dihydroxyphenyl)-5-chloro-benzotriazole represented by the formula (A-1), and if necessary at least one antioxidant selected from the group consisting of hindered phenol antioxidants and hindered amine antioxidants.

The present invention will be explained in more detail as follows by referring partly to the accompanying drawings wherein.

The triazole compound of the formula A-1 is a novel compound and can be prepared by the following methods.

Preparation Method 1

4-Chloro-2-nitraniline (II) is diazotized at $-5°$ C. to 20° C. with sodium nitrite and coupled with resorcin (III) in an aqueous medium of pH 1 to 7, preferably 1 to 3, at $-5°$ C. to 20° C. for 5 to 20 hours to obtain 4-chloro-2-nitro-2',4'-dihydroxyazobenzene (IV). The nitroazo compound (IV) thus obtained is added to 2 to 30 % aqueous sodium hydroxide solution, a reducing agent such as metals (zinc, tin and iron) is added thereto, and then the mixture is heated at 30° C. to 90° C. for 1 to 10 hours to obtain the objective compound (A-1). The reaction proceeds according to the following scheme.

Preparation Method 2

The nitro compound (IV) is added to a 2 to 20 % aqueous sodium hydroxide solution and a reducing agent such as glucose, ammonium sulfide, sodium sulfide and sodium hydrogen sulfide is added thereto. Then, the mixture is heated at 20° C. to 40° C. for 3 to 6 hours, and thereafter metal (zinc, aluminum, tin or iron) is added. The mixture is maintained at 0° C. to 30° C. for 1 to 5 hours to obtain the objective compound (A-1). The reaction proceeds according to the following scheme.

-continued

(A-1)

Figure 1:
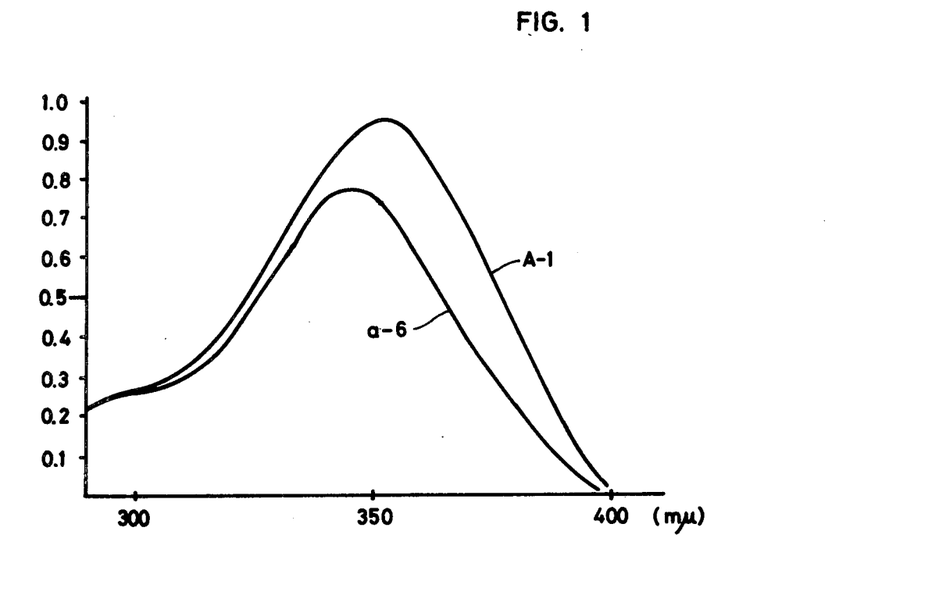
FIG. 1 shows the ultraviolet absorption curves of the present compound (A-1) and the well-known compound (a-6). The diagrams were plotted, with absorption coefficient (10 mg./1/EtOH) as ordinate and wavelength (mμ) as abscissa.

The resulting compound (A-1), which has a maximum absorption at 354 mμ (in $C_2H_5OH$), has the excellent property of exhibiting a strong absorption to rays having a wave length range of 310 – 380 mμ among ultraviolet rays (300 – 400 mμ) which rays deteriorate or degrade organic substances, particularly polyurethane resins, but no absorption in the range of above 400 mμ, so that it has a strong protective effect against the adverse influence of ultraviolet rays and gives almost no coloration (refer to FIG. 1 and Table 1).

Table 1

| Comparison of absorbing power (10 mg./l. $C_2H_5OH$) | | |
|---|---|---|
| | maximum absorption | |
| | (mμ) | a |
| Present compound (A-1) | 354 | 93.7 |
| Commerically available compound* | 343 | 79.1 |
| Commercially available compound** | 342 | 72.0 |

Note:  a: absorptivity in liters per g.-cm.

Therefore, the present compound, i.e. the present ultraviolet absorber, functions very effectively even in a trace amount of 0.001 % by weight based on polyurethane resins, and moreover has the excellent property that it does not give a yellow coloration or staining to the resins even when used in a large amount. Other characteristics of the present compound are a good compatibility with and affinity for polyurethane resins and a high resistance to sublimation by heat.

Furthermore, the inventors have conducted studies to find a method of protecting polyurethane resins from degradation due to ultraviolet ray, and have found on the basis of such studies; the fact that the degradation is not a pure photodegradation, but a photodegradation including oxidation, that, by combining the present compound (A-1) (referred to as A-component hereinafter) with at least one antioxidant selected from the group consisting of hindered phenol antioxidants (referred to as B-component hereinafter) and hindered amine antioxidants (referred to as C-component hereinafter), polyurethane compositions having the superior photostability can be obtained which is not achieved with the individual components.

The B-component includes a compound represented by the formulae;

wherein X is a $C_1 - C_{18}$ alkyl, $C_1 - C_8$ alkylene, $-(CH_2)_4C$ or mono-, di- or tri-$C_1 - C_5$ alkyleneamine group, Y is $C_1 - C_8$ alkylene, $C_4 - C_{18}$ alkylidene group or a sulfur atom, $R_1$ and $R_2$ are each a hydrogen atom or $C_1 - C_4$ alkyl group and $R_1$ and $R_2$ may be the same or different, $R_3$, $R_4$ and $R_5$ are each $C_1 - C_{18}$ alkyl group and $R_3$, $R_4$ and $R_5$ may be the same or different, n is an integer of 1 to 4 and m is an integer of 1 to 5. Of these, tetrakis[methylene(3,5-di-t-butyl-4-hydroxy-hydrocinnamate)]-methane, and N,N,N-tris[β-(3,5-di-t-butyl-4-hydroxyphenyl)-propionyl]-tripropanolamine are favorably used.

The C-component includes a compound represented by the formulas;

wherein $R_6$ is $C_1 - C_{18}$ alkyl, aryl, aralkyl or $C_6 - C_{12}$ cycloalkyl group, $R_7$, $R_8$, $R_9$ and $R_{10}$ are independently a hydrogen atom or a $C_1 - C_8$ alkyl or alkoxy group, $R_{11}$, $R_{12}$, $R_{13}$, $R_{14}$, $R_{15}$, $R_{16}$, $R_{17}$ and $R_{18}$ are independently a hydrogen atom or a $C_1 - C_{18}$ alkyl group, and $n'$ is an integer of 1 to 3. Of these, 4-benzoyloxy-2,2,6,6-tetramethyl-piperidine and 2,2,4-trimethyl-1,2-dihydroquinoline polymer are favorably used.

The present compound (A-1) exhibits an outstanding synergistic effect in protecting polyurethane resins by the combination with at least one antioxidant selected from the group consisting of B- and C-components, unlike the presently commercially available ultraviolet absorbers.

The present compound, i.e. the present ultraviolet absorber and the mixture thereof with at least one antioxidant selected from the group consisting of the B- and O-components (the mixture being referred to as a mixed ultraviolet stabilizer) can be applied to polyurethane resins according to the conventional well-known methods. The present absorber and mixed ultraviolet stabilizer may contain other additives such as softening agents, antioxidants other than those used in the present invention, thermal stabilizers and pigments.

The amount of the present absorber used is 0.001 to 10 % by weight, preferably 0.05 to 3.0 % by weight, based on solid polyurethane resin, and the amount of the present mixed ultraviolet stabilizer is 0.003 to 10 % by weight, preferably 0.1 to 3.0 % by weight, based on solid polyurethane resin.

In the present mixed ultraviolet stabilizer, the weight ratio of A-component to B and/or C component is 1:9 – 9:1, preferably 1:1 – 1:4.

The present invention will be illustrated specifically with reference to the following examples which are only given for the purpose of illustration and not to be interpreted as limiting thereto.

i. Preparation of 4-chloro-2-nitro-2',4'-dihydroxyazobenzene.

In 616 g. of a 17.5 % hydrochloric acid are dissolved at 70 to 80° C. 121 g. of 4-chloro-2-nitroaniline and the resulting solution is added to 300 g. of ice at a time while thoroughly stirring. Diazotization is carried out by adding a solution of 51.0 g. of sodium nitride in 70 g. of water to the above solution at below 0° C. separately, 81.1 g. of resorcin are dissolved in a mixture of 510 g. of a 35 % hydrochloric acid and 1750 g. of ice water, and then the resulting solution is kept at about 0° C. Then, the diazo liquor obtained above is added dropwise to the resorcin solution at about 0° C. over about 1.5 hours. After completion of the addition, the solution is stirred at the same temperature for further 1 hour and then kept at 50° C. for 1 hour. Thus the coupling reaction is completed. Separated red 4-chloro-2-nitro-2',4'-dihydroxyazobenzene is filtered, thoroughly washed with water and dried. The amount obtained is 197.1 g. (yield 96.0 %).

ii. Preparation of 5-chloro-2-(2',4'-dihydroxyphenyl)-benzotriazole.

To a suspension of 29.3 g. of 4-chloro-2-nitro-2',4'-dihydroxy-azobenzene thus obtained in 100 g. of methanol are added 50 g. of a 40 % aqueous caustic soda solution and then 25.5 g. of zinc powder at room temperature. On heating the reaction solution under reflux for about 1 hour, the solution changes in color. Thereafter, the solution is further heated for 30 minutes and filtered hot. The filtrate is neutralized with acetic acid at about 10° C. to separate a solid matter. The matter is filtered, dried and recrystallized from toluene repeatedly to obtain pale yellow 5-chloro-2-(2',4'-dihydroxyphenyl)-benzotriazole in a yield of 60 % (m.p. 188° – 189° C.).

In the following examples, commercially available ultraviolet absorbers were also tested as the A-component in order to compare with the present compound. These absorbers were abbreviated as follows in the examples. The hindered phenol antioxidants (B-component) and hindered amine antioxidants (C-component) were likewise abbreviated.

Ultraviolet absorbers (A-component):

| Abbreviation | $R_1$ | $R_2$ | $R_3$ | X | Remarks |
|---|---|---|---|---|---|
| A-1 | H | OH | H | Cl | the present compound |
| a-2 | H | H | $CH_3$ | H | reference compound |
| a-3 | $C_5H_{11}$ | H | $C_5H_{11}$ | H | " |
| a-4 | $tC_4H_9$ | H | $tC_4H_9$ | Cl | " |
| a-5 | H | OH | H | H | " |
| a-6 | H | $OC_8H_{17}$ | H | H | " |

Hindered phenol antioxidants (B-component):

| Abbreviation | Chemical formula |
|---|---|
| B-1 | tetrakis[methylene(3,5-di-t.-butyl-4-hydroxy-hydrocinnamate)]-methane |
| B-2 | N,N,N-tris[β-(3,5-di-t.-butyl-4-hydroxyphenyl)-propionyl]-tripropanol amine |
| B-3 | 1,3,5-trimethyl-2,4,6-tris(3,5-di-t.-butyl-4-hydroxybenzyl)-benzene |
| B-4 | 2,2'-methylene-bis-(6-t.-butyl-4-methylphenol) |
| B-5 | 2,6-di-t.-butyl-4-methylphenol |
| B-6 | 4,4'-butylidene-bis-(6-t.-butyl-3-methylphenol) |
| B-7 | 2,6-di-stearyl-4-methylphenol |
| B-8 | 3,5-di-t.-butyl-4-hydroxy-hydrocinnamate stearyester |
| B-9 | 4,4'-thiohis-(6-t.-butyl-3-methylphenol) |
| B-10 | 4,4'-methylene-bis-(2,6-di-t.-butylphenol) |

Hindered amine antioxidants (C-component):

| Abbreviation | Chemical formula |
|---|---|
| C-1 | 4-benzoyloxy-2,2,6,6-tetramethyl-piperidine |
| C-2 | 2,2,4-trimethyl-1,2-dihydroquinoline polymer (Antigene RD-F, trademark of Sumitomo Chemical Co., Ltd.) |
| C-3 | 6-ethoxy-2,2,4-trimethyl-1,2-dihydroquinoline |
| C-4 | trimethyl-dihydroquinoline derivative (Antigene MW, trademark of Sumitomo Chemical Co., Ltd.) |
| C-5 | phenothiazine |
| C-6 | bis-(2,2,6,6-tetramethyl-4-piperidyl)sebacate |

Example 1

Lightfastness test of polyurethane applied with the present compound (antiyellowing test)

Blending ratio:

| polyurethane resin | 100 parts |
|---|---|
| ultraviolet absorber | X parts |

Preparation of test sample:

To a 25 % urethane dope (a mixture of 25 parts of polyurethane resin, 3.75 parts of dimethylformamide (DMF) and 71.25 parts of tetrahydrofuran (THF)) was added the present compound in the above blending ratio to make a coating liquor. The liquor was applied on nylon film which was then dried at 45° C. in an oven for 1 hour. The coated film was taken as a test piece (10 cm. × 5 cm.).

Exposure condition:
Fade-O-meter (Toyo Seiki Co.)
Test results of antiyellowing effect on polyurethane.

Table 2

| Ultraviolet absorber | x (part) | Lightfastness Exposure time (hr.) | | | | | Change in appearance |
|---|---|---|---|---|---|---|---|
| | | 0 | 23 | 46 | 69 | 92 | |
| No addition | 0 | 0 | 4–5 | 6 | 7–8 | 9 | high yellowing (yellowish-brown) |
| Present compound (A-1) | 1.0 | 0 | 2 | 3 | 3–4 | 4–5 | |
| | 1.5 | 0 | 1–2 | 2–3 | 3 | 3–4 | |
| | 2.0 | 0 | 1–2 | 2 | 2–3 | 3–4 | |
| Well known compound (a-6) | 1.0 | 0 | 3 | 4–5 | 6 | 7–8 | high yellowing |
| | 1.5 | 0 | 2–3 | 4 | 5 | 6–7 | high yellowing, high blooming |
| | 2.0 | 0 | 2–3 | 4–5 | 5–6 | 6–7 | high yellowing, high blooming |
| Well known compound (a-2) | 1.0 | 0 | 3–4 | 4–5 | 6 | 7 | high yellowing, high blooming |
| | 1.5 | 0 | 3 | 4 | 4–5 | 6 | high yellowing, high blooming |
| | 2.0 | 0 | 3 | 3–4 | 4–5 | 5–6 | high yellowing, high blooming |
| Well known compound (a-5) | 1.0 | 0 | 3 | 5 | 6–7 | 8 | high yellowing |
| | 1.5 | 0 | 2–3 | 3–4 | 5–6 | 7 | high yellowing |
| | 2.0 | 0 | 2 | 3 | 4–5 | 6 | high yellowing |

Note:
The lightfastness and change in appearance were evaluated visually. Larger numbers mean a larger degree of discoloration.

Figure 2:
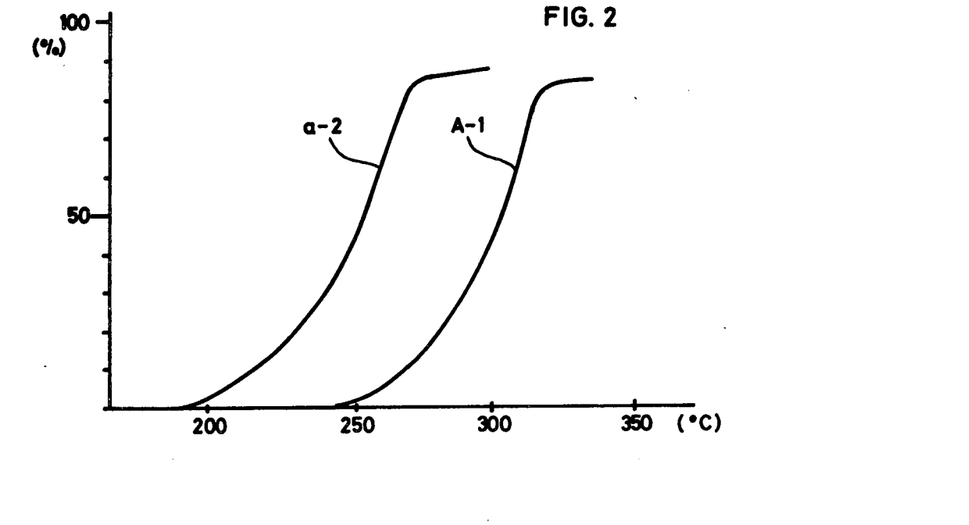
FIG. 2 shows graphically the results of volatility measurement on a thermobalance, with loss in weight (%) as ordinate and temperature (° C.) as abscissa. The standard differential thermobalance (Rigaku Denki Co.) was used for the measurement.

As can be seen from the test results, the present compound has an extremely superior antiyellowing effect on polyurethane. The present compound was also measured for the volatility on a thermobalance, and was found to be very low as compared with the compound (a-2) similar to the present compound (refer to FIG. 2).

Example 2

Urethane resin and the present compound of 0.01 % by weight based on the resin were thoroughly kneaded at 150° C. on a heating roll and then molded into a required shape on a mold, press or injection molding machine. The molding thus obtained was extremely stable with no danger of discoloration as compared with molding not containing the present compound. That is, films which had been prepared as above with and without the compounds in Table 3, were exposed to sunlight for 100 and 300 hours, and measured visually on the appearance before and after the exposure. The results are as shown in Table 3.

Table 3

| Compounds | Film appearance after exposure | |
|---|---|---|
| | 100 hrs. | 300 hrs. |
| Present compound (a-1) | no change | no change |
| Well known compound (a-2) | slightly yellowish | yellowish brown |
| Blank | deep yellowish brown | deep black brown |

Furthermore, the sheet having the present compound incorporated showed a remarkably reduced tendency towards brittleness after weathering than the sheets not containing the present compound.

Example 3

Lightfastness test of polyurethane applied with the mixed ultraviolet stabilizer according to the present invention (antiyellowing effect) Blending ratio:

| polyurethane resin | 100 parts |
|---|---|
| mixed ultraviolet stabilizer: | |
| A-component | x parts |
| B-component | y parts |
| C-component | z parts |

Preparation of test sample:

To a 25 % urethane dope (a mixture of 25 parts of polyurethane resin, 3.75 parts of dimethylformamide (DMF) and 71.25 parts of tetrahydrofuran (THF) was added the present mixed ultraviolet stabilizer in the above blending ratio to make a coating liquor. The liquor was applied on nylon film which was then dried at 45° C. in an oven for 1 hour. The coated film was taken as a test piece (10 cm. × 5 cm.).

Exposure condition:
Fade-O-meter (Toyo Seiki Co.)
Test results of antiyellowing effect on polyurethane are as shown in Table 4.

Table 4

| No. | Additives and amounts | | | | | | Light fastness after exposure (grade) | | | | |
|---|---|---|---|---|---|---|---|---|---|---|---|
| | A-component | | B-component | | C-component | | Exposure time (hr.) | | | | |
| | | x | | y | | z | 0 | 45 | 90 | 120 | 150 |
| 1 | — | | — | | — | | 0 | 6 | 9 | 10 | 10 |
| 2 | A-1 | 1.0 | — | | — | | 0 | 3 | 4–5 | 6–7 | 8–9 |
| 3 | " | 0.5 | B-2 | 0.25 | C-2 | 0.25 | 0 | 0–1 | 1–2 | 2 | 2–3 |
| 4 | A-1 | 0.5 | B-1 | 0.5 | — | | 0 | 0–1 | 2–3 | 4–5 | 6 |
| 5 | " | " | — | | C-1 | 0.5 | 0 | 0–1 | 2–3 | 4–5 | 6 |
| 6 | " | " | — | | C-2 | 0.5 | 0 | 0–1 | 2–3 | 4–5 | 6 |
| 7 | " | " | B-1 | 0.25 | C-1 | 0.25 | 0 | 0–1 | 1–2 | 2 | 2–3 |
| 8 | " | " | B-8 | " | C-5 | " | 0 | 0–1 | 1–2 | 2–3 | 3 |
| 9 | " | " | B-2 | " | C-3 | " | 0 | 0–1 | 2–3 | 4–5 | 5 |
| 10 | " | " | B-4 | " | C-2 | " | 0 | 0–1 | 2 | 3–4 | 5 |
| 11 | " | " | B-5 | " | C-2 | " | 0 | 0–1 | 2–3 | 4–5 | 5 |
| I | a-2 | 1.0 | — | | — | | 0 | 4–5 | 7 | 8–9 | 10 |
| II | " | 0.5 | B-2 | 0.25 | C-2 | 0.25 | 0 | 3 | 4–5 | 6–7 | 9 |
| III | a-3 | 1.0 | — | | — | | 0 | 4 | 6 | 8 | 9 |
| IV | " | 0.5 | B-2 | 0.25 | C-2 | 0.25 | 0 | 1–2 | 3–4 | 5 | 6 |
| V | a-4 | 1.0 | — | | — | | 0 | 4–5 | 6–7 | 8–9 | 9–10 |
| VI | " | 0.5 | B-2 | 0.25 | C-2 | 0.25 | 0 | 3 | 5 | 6 | 6 |

Table 4-continued

| No. | Additives and amounts | | | | | | Light fastness after exposure (grade) | | | | |
|---|---|---|---|---|---|---|---|---|---|---|---|
| | A-component | | B-component | | C-component | | Exposure time (hr.) | | | | |
| | x | | y | | z | | 0 | 45 | 90 | 120 | 150 |
| VII | a-5 | 1.0 | — | | — | | 0 | 5 | 8 | 10 | 10 |
| VIII | " | 0.5 | B-2 | 0.25 | C-2 | 0.25 | 0 | 3–4 | 5–6 | 8 | 9 |
| IX | a-6 | 1.0 | — | | — | | 0 | 4–5 | 7–8 | 9 | 10 |
| X | " | 0.5 | B-2 | 0.25 | C-2 | 0.25 | 0 | 2–3 | 5–6 | 7 | 8 |

Note:
The lightfastness after exposure was evaluated visually based on the degree of discoloration of test pieces, taking the control (untested piece) as 0 and the black brown-colored test piece as 10.

It was found from Table 4 that the present compound has an excellent synergistic effect in protecting polyurethane resins from ultraviolet radiation.

Example 4

Polyurethane dope was prepared in the same manner as described in Example 1, and formed into sheet of 0.1 mm. thick. Test pieces were cut off from the sheet by means of the No. 3 dumb-bell and exposed in the Fade-O-meter (Toyo seiki Co.) for a required period of time. After the exposure, the test pieces were subjected to a tension test under the following conditions in order to measure the elongation retention and breaking strength retention. The results are as shown in Tables 5 and 6.

Tension test condition:

| extensometer (Toyo Seiki Co.) | |
|---|---|
| tension rate | 10 mm./min. |
| tension temperature | 20 ± 0.5° C. |
| gauge length | 20 mm. |

Table 5

| Exp. No. | Additives and amounts | | | | | | Elongation retention (%) | | | | |
|---|---|---|---|---|---|---|---|---|---|---|---|
| | A-component | | B-component | | C-component | | Lightfastness after exposure | | | | |
| | | | | | | | Exposure time (hr.) | | | | |
| | x | | y | | z | | 0 | 45 | 90 | 120 | 150 |
| 1 | — | | — | | — | | 100 | 24.5 | 18.0 | 16.7 | — |
| 2 | A-1 | 1.0 | — | | — | | 100 | 60.3 | 45.6 | 31.7 | 16.7 |
| 3 | " | 0.5 | B-1 | 0.25 | C-1 | 0.25 | 100 | 96.8 | 76.7 | 58.5 | 45.3 |
| 4 | " | " | B-2 | " | C-2 | " | 100 | 95.9 | 75.3 | 54.9 | 42.1 |
| 5 | A-1 | 0.5 | B-1 | 0.25 | C-3 | 0.25 | 100 | 93.1 | 70.3 | 51.4 | 39.9 |
| 6 | " | " | B-10 | " | C-2 | " | " | 88.3 | 69.1 | 51.3 | 32.4 |
| I | a-2 | 1.0 | — | | — | | " | 51.1 | 36.3 | 23.8 | 9.8 |
| II | " | 0.5 | B-1 | 0.25 | C-1 | 0.25 | " | 59.4 | 43.1 | 28.0 | 15.4 |
| III | " | " | B-2 | " | C-2 | " | " | 60.3 | 45.2 | 30.0 | 18.7 |
| IV | a-3 | 1.0 | — | | — | | " | 55.5 | 41.3 | 28.7 | 14.3 |
| V | " | 0.5 | B-1 | 0.25 | C-1 | 0.25 | " | 73.1 | 55.9 | 41.3 | 29.9 |
| VI | " | " | B-2 | " | C-2 | " | " | 75.0 | 57.6 | 43.2 | 31.4 |
| VII | a-5 | 1.0 | — | | — | | " | 51.3 | 31.3 | 19.9 | 7.3 |
| VIII | " | 0.5 | B-1 | 0.25 | C-1 | 0.25 | " | 60.1 | 40.1 | 27.3 | 14.6 |
| IX | " | " | B-2 | " | C-2 | " | " | 61.3 | 41.4 | 29.0 | 15.9 |

Note:
x, y and z in the Table are the same as in Table 3.

Table 6

| Exp. No. | Additives and amounts | | | | | | Breaking strengh retention (%) | | | | |
|---|---|---|---|---|---|---|---|---|---|---|---|
| | A-component | | B-component | | C-component | | Lightfastness after exposure | | | | |
| | | | | | | | Exposure time (hr.) | | | | |
| | x | | y | | z | | 0 | 45 | 90 | 120 | 150 |
| 1 | — | | — | | — | | 100 | 21.3 | 13.4 | 10.0 | — |
| 2 | A-1 | 1.0 | — | | — | | " | 54.4 | 40.3 | 25.7 | 9.8 |
| 3 | " | 0.5 | B-1 | 0.25 | C-1 | 0.25 | " | 90.9 | 70.8 | 52.8 | 40.0 |
| 4 | " | " | B-2 | " | C-2 | " | " | 90.0 | 69.9 | 51.3 | 38.0 |
| 5 | A-1 | 0.5 | B-2 | 0.5 | — | | " | 75.3 | 54.3 | 39.9 | 24.6 |
| 6 | " | " | — | | C-2 | 0.5 | " | 74.1 | 53.2 | 38.0 | 23.9 |
| 7 | " | " | B-10 | 0.25 | C-2 | 0.25 | " | 83.4 | 65.0 | 46.0 | 27.8 |
| I | a-2 | 1.0 | — | | — | | " | 41.0 | 26.3 | 13.8 | 5.4 |
| II | " | 0.5 | B-1 | 0.25 | C-1 | 0.25 | " | 50.0 | 33.3 | 18.4 | 7.0 |
| III | " | " | B-2 | " | C-2 | " | " | 50.1 | 35.3 | 20.1 | 8.7 |
| IV | a-3 | 1.0 | — | | — | | " | 45.5 | 31.3 | 18.0 | 4.3 |
| V | " | 0.5 | B-1 | 0.25 | C-1 | 0.25 | " | 63.0 | 45.6 | 31.3 | 20.1 |
| VI | " | " | B-2 | " | C-2 | " | " | 65.3 | 47.8 | 33.4 | 21.1 |
| VII | a-5 | 1.0 | — | | — | | " | 41.3 | 21.1 | 10.9 | 3.1 |
| VIII | " | 0.5 | B-1 | 0.25 | C-1 | 0.25 | " | 50.7 | 30.6 | 17.6 | 7.3 |
| IX | " | " | B-2 | " | C-2 | " | " | 50.3 | 30.3 | 20.0 | 7.8 |

Example 5

To a mixture of 10 parts of methylene-bis-(4-phenylisocyanate), 0.2 part of (A-1), 0.1 part of (B-10) and 0.1 part of (C-6) were added 19 parts of polyoxytetramethylene glycol (M.W. 954). The resulting mixture was reacted at 85° C. for 60 minutes to obtain an intermediate polymer which was almost colorless and transparent.

The polymer was dissolved in 90 parts of dimethylformamide and to the resulting solution was added a solution of 1.4 part of 1,2-propylenediamine in 30 parts of dimethylformamide at 0° C. while stirring. On reacting for some time, the reaction solution became a highly viscous elastomer solution which was then melt-spun through a nozzle of 0.1 mm. in diameter into a cylinder kept at 180° C. Thus, elastic yarn of good performance was obtained.

The elastic yarn thus obtained was exposed in the Fade-O-meter and then measured for the tenacity (g./denier). The results are shown in Table 6 together with those obtained using (a-3) in place of (A-1) and no components. Table 7 shows that the present compound gives an excellent lightfastness.

Table 7

| Exp. No. | Additives A-component | B-component | C-component | Tenacity after exposure (g./denier) Exposure time (hr.) | | |
|---|---|---|---|---|---|---|
| | | | | 0 | 40 | 60 |
| 1 | — | — | — | 0.80 | 0.47 | 0.13 |
| 2 | A-1 | — | — | 0.91 | 0.78 | 0.70 |
| 3 | A-1 | B-10 | C-6 | 0.92 | 0.90 | 0.88 |
| I | a-3 | B-10 | C-6 | 0.90 | 0.68 | 0.59 |
| II | a-3 | — | — | 0.90 | 0.62 | 0.25 |

Example 6

A mixture of 800 parts of polytetramethylene ether diol (M.W. 1,010), 17.4 parts of N,N-bis-($\beta$-hydroxypropyl)-N-methylamine, 306.6 parts of diphenyl methane-4,4'-diisocyanate and 284 parts of chlorobenzene was heated at 65 to 70° C. for 52 minutes and then cooled to room temperature to obtain a NCO prepolymer solution (1.88 % NCO). Four hundred parts of the solution thus obtained were added for 4 minutes, while vigorously stirring, to a suspension which had been freshly prepared by adding 15 parts of solid carbon dioxide to a solution of 5.93 parts of ethylenediamine in 898 parts of dimethylformamide. Thus, a homogeneous, viscous and slightly yellow elastomer solution was obtained.

The solution thus obtained was colored with rutile titanium dioxide of 4 % by weight based on the solid elastomer of the solution. According to the usual methods, the colored solution (viscosity 423 poise) was formed into film with and without addition of the three components (A-component x %, B-component Y % and C-component z % based on the solid elastomer). The film was cut into filament and exposed to ultraviolet radiation in the Fade-O-meter. The tenacity of the filament after exposure is as shown in Table 8.

hydroxypropyl)-N-methylamine, 306.6 parts of diphenyl methane-4,4'-diisocyanate and 284 parts of chlorobenzene was heated at 65 to 70° C. for 50 minutes and then cooled to room temperature to obtain a NCO prepolymer solution (1.9 % NCO). Eight hundred parts of the prepolymer solution thus obtained were mixed with a solution of 38.7 parts of 4,4'-diamino-diphenylmethane in 1872 parts of dimethylformamide and after stirring for 12 hours, 3.38 parts of diphenylmethane-4,4'-diisocyanate were further added thereto to obtain a viscous elastomer solution (102 poise/20° C.).

The elastomer solution was treated with 1 part of acetic acid anhydride per 100 parts of the solution, and then colored with rutile titanium dioxide of 4% by weight based on the solid elastomer of the solution. The colored solution was applied on glass plate with and without addition of the three components ((A-1) 1%, (B-5) 0.5% and (C-3) 0.5% based on the solid elastomer), and dried at 100° C. for 60 minutes to obtain films of 0.15 to 0.20 mm. thick. The loaded and unloaded films thus obtained were exposed in the Fade-O-meter and then measured for the degree of coloration after exposure visually. The film loaded with the present compound showed a remarkably less degree of coloration than the unloaded film. The same result was also obtained with the film loaded with (B-4) and (C-4) in place of (B-5) and (C-3), respectively.

Example 8

A mixture of 800 parts of polytetramethylene ether diol (M.W. 1,010), 17.4 parts of N,N,-bis-($\beta$-hydroxypropyl)-N-methylamine, 306.6 parts of 4,4'-diphenylmethane-4,4'-diisocyanate and 284 parts of chlorobenzene was heated at 65° to 70° C. for 52 minutes and then cooled to room temperature to obtain a NCO prepolymer solution (1.88% NCO). Four hundred parts of the solution thus obtained were added for 4 minutes, while vigorously stirring, to a suspension which had been freshly prepared by adding 15 parts of solid carbon dioxide to a solution of 5.93 parts of ethylenediamine in 898 parts of dimethylformamide. Thus, a homogeneous, viscous and slightly yellow elastomer solution was obtained.

The solution thus obtained was colored with rutile titanium dioxide of 4% by weight based on the solid elastomer of the solution. According to the method described in Example 7, the colored solution (viscosity 423 poise) was formed into film with and without addition of the compounds as shown in Table 9. The film thus obtained was cut into filaments, exposed to ultraviolet radiation in the Fade-O-meter and measured for Table 8

| Exp. No. | Additives A-component | | B-component | | C-component | | Tenacity after exposure (g./denier) Exposure time (hr.) | | | | |
|---|---|---|---|---|---|---|---|---|---|---|---|
| | | x | | y | | z | 0 | 20 | 40 | 60 | 80 |
| 1 | — | | — | | — | | 0.60 | 0.05 | — | — | — |
| 2 | A-1 | 4 | — | | — | | " | 0.4 | 0.3 | 0.1 | — |
| 3 | " | 2 | B-2 | 1 | C-2 | 1 | " | 0.6 | 0.6 | 0.58 | 0.4 |
| 4 | " | 2 | B-8 | 2 | — | | " | 0.59 | 0.53 | 0.45 | 0.35 |
| I | a-3 | 4 | — | | — | | " | 0.3 | 0.1 | — | — |
| II | " | 2 | B-2 | 1 | C-2 | 1 | " | 0.4 | 0.3 | 0.1 | — |
| III | " | 2 | B-8 | 2 | — | | " | 0.37 | 0.25 | 0.09 | — |

Example 7

A mixture of 800 parts of polytetramethylene ether diol (OH number 111), 17.4 parts of N,N-bis-($\beta$- the tenacity (g./denier). The results are as shown in Table 9.

Table 9

| Exp. No. | Additives and amounts | | | | | | Tenacity after exposure | | | | |
|---|---|---|---|---|---|---|---|---|---|---|---|
| | A-component | | B-component | | C-component | | Exposure time (hr.) | | | | |
| | | x | | y | | z | 0 | 20 | 40 | 60 | 80 |
| 1 | — | | — | | — | | 0.60 | 0.04 | — | — | — |
| 2 | A-1 | 4 | — | | — | | " | 0.46 | 0.38 | 0.30 | 0.27 |
| 3 | " | 2 | B-2 | 1 | C-3 | 1 | " | 0.60 | 0.59 | 0.58 | 0.50 |
| 4 | " | " | B-4 | 2 | — | | " | 0.52 | 0.40 | 0.35 | 0.33 |
| 5 | A-1 | 2 | B-2 | 1 | C-4 | 1 | " | 0.59 | 0.58 | 0.52 | 0.49 |
| 6 | " | " | B-8 | 2 | — | | " | 0.53 | 0.43 | 0.38 | 0.32 |
| I | a-3 | 4 | — | | — | | " | 0.41 | 0.34 | 0.25 | 0.20 |
| II | " | 2 | B-2 | 1 | C-3 | 1 | " | 0.55 | 0.50 | 0.40 | 0.38 |
| III | " | " | B-4 | 2 | — | | " | 0.45 | 0.37 | 0.27 | 0.21 |

Note:
x, y and z in the table are the same as in Example 3, and are parts by weight based on 100 parts of solid elastomer.

What is claimed is:

1. A stabilized polyurethane resin composition comprising (1) a polyurethane resin and (2) a stabilizing amount of an ultraviolet absorber of the formula (A-1), or a mixed ultraviolet stabilizer comprising the ultraviolet absorber (A-1) and an antioxidant which is selected from the group consisting of hindered phenols and hindered amines, said hindered phenol antioxidant being a compound of the formula, wherein X is a $C_1 - C_{18}$ alkyl, $C_1 - C_8$ alkylene, $-(CH_2)_4C$ or mono-, di- or tri-$C_1 - C_5$ alkyleneamine group, Y is a $C_1 - C_8$ alkylene, $C_4 - C_{18}$ alkylidene group or a sulfur atom, $R_1$ and $R_2$ are each a hydrogen atom or $C_1 - C_4$ alkyl group and $R_1$ and $R_2$ may be the same or different, $R_3$, $R_4$ and $R_5$ are each $C_1 - C_{18}$ alkyl group and $R_3$, $R_4$ and $R_5$ may be the same or different, n is an integer of 1 to 4 and m is an integer of 1 to 5 and said hindered amine antioxidant being a compound of the formula, wherein $R_6$ is a $C_1 - C_{18}$ alkyl, aryl, aralkyl or $C_6 - C_{12}$ cycloalkyl group, $R_7$, $R_8$, $R_9$ and $R_{10}$ are independently a hydrogen atom or a $C_1 - C_8$ alkyl or alkoxy group, $R_{11}$, $R_{12}$ $R_{13}$, $R_{14}$, $R_{15}$, $R_{16}$, $R_{17}$ and $R_{18}$ are independently a hydrogen atom or a $C_1 - c_{18}$ alkyl group, and n' is 1 and wherein the weight ratio of the ultraviolet absorber (A-1) to the antioxidant is 1:9 to 9:1.

2. The composition of claim 1, wherein the antioxidant is tetrakis[methylene (3,5-di-t-butyl-4-hydroxyhydrocinnamate) ]-methane or N,N,N-tris[β-(3,5-di-5-butyl-4-hydroxyphenyl)-propionyl]-tripropanolamine.

3. The composition of claim 1, wherein the antioxidant is 4-benzoyloxy-2,2,6,6-tetramethyl-piperidine or 2,2,4-trimethyl-1,2-dihydroquinoline.

4. The composition of claim 1, wherein the amount of the ultraviolet absorber is 0.001 to 10% by weight based on the weight of polyurethane resin.

5. The composition of claim 1, wherein the amount of the mixed ultraviolet stabilizer is 0.003 to 10% by weight based on the weight of polyurethane resin.

6. A shaped article prepared from the stabilized polyurethane resin of claim 1.

7. A stabilized polyurethane resin composition comprising (1) a polyurethane resin and (2) a stabilizing amount of a mixed ultraviolet stabilizer comprising
   a. a ultraviolet absorber of the formula (A-1), b. a hindered phenol antioxidant and (c) a hindered amine antioxidant, said hindered phenol antioxidant being a compound of the formula wherein X is a $C_1 - C_{18}$ alkyl, $C_1 - C_8$ alkylene, $-(CH_2)_4C$ or mono-, di- or tri-$C_1 - C_5$ alkyleneamine group, Y is a $C_1 - C_8$ alkylene, $C_4 - C_{18}$ alkylidene group or a sulfur atom, $R_1$ and $R_2$ are each a hydrogen atom or $C_1 - C_4$ alkyl group and $R_1$ and $R_2$ may be the same or different, $R_3$, $R_4$ and $R_5$ are each $C_1 - C_{18}$ alkyl group and $R_3$, $R_4$ and $R_5$ may be the same or different, $n$ is an integer of 1 to 4 and $m$ is an integer of 1 to 5 and said hindered amine antioxidant being a compound of the formula, wherein $R_6$ is a $C_1 - C_{18}$ alkyl, aryl, aralkyl or $C_6 - C_{12}$ cycloalkyl group, $R_7$, $R_8$, $R_9$ and $R_{10}$ are independently a hydrogen atom or a $C_1 - C_8$ alkyl or alkoxy group, $R_{11}$, $R_{12}$, $R_{13}$, $R_{14}$, $R_{15}$, $R_{16}$, $R_{17}$ and $R_{18}$ are independently a hydrogen atom or a $C_1 - C_{18}$ alkyl group, and $n'$ is 1 and wherein the weight ratio of the ultraviolet absorber (A-1) to the antioxidant is 1:9 to 9:1.

8. A mixed ultraviolet stabilizer for stabilizing polyurethane resins against ultraviolet rays, comprising an ultraviolet absorber of the formula (A-1)

and an antioxidant selected from the group consisting of hindered phenol antioxidants and hindered amine antioxidants, said hindered phenol being a compound of the formula wherein X is a $C_1 - C_{18}$ alkyl, $C_1 - C_8$ alkylene, $-(CH_2)_4C$ or mono-, di- or tri-$C_1 - C_5$ alkyleneamine group, Y is a $C_1 - C_8$ alkylene, $C_4 - C_{18}$ alkylidene group or a sulfur atom, $R_1$ and $R_2$ are each a hydrogen atom or $C_1 - C_4$ alkyl group and $R_1$ and $R_2$ may be the same or different, $R_3$, $R_4$ and $R_5$ are each $C_1 - C_{18}$ alkyl group and $R_3$, $R_4$ and $R_5$ may be the same or different, n is an integer of 1 to 4 and m is an integer of 1 to 5 and said hindered amine antioxidant being a compound of the formula, wherein $R_6$ is a $C_1 - C_{18}$ alkyl, aryl, aralkyl or $C_6 - C_{12}$ cycloalkyl group, $R_7$, $R_8$, $R_9$ and $R_{10}$ are independently a hydrogen atom or a $C_1 - C_8$ alkyl or alkoxy group, $R_{11}$, $R_{12}$, $R_{13}$, $R_{14}$, $R_{15}$, $R_{16}$, $R_{17}$ and $R_{18}$ are independently a hydrogen atom or a $C_1 - C_{18}$ alkyl group, and $n'$ is 1 and wherein the weight ratio of the ultraviolet absorber (A-1) to the antioxidant is 1:9 to 9:1.

9. A mixed ultraviolet stabilizer for stabilizing polyurethane resins against ultraviolet rays, comprising
a. an ultraviolet absorber of the formula (A-1)

(A-1)

b. a hindered phenol antioxidant and (c) a hindered amine antioxidant, said hindered phenol antioxidant being a compound of the formula wherein X is a $C_1 - C_{18}$ alkyl, $C_1 - C_8$ alkylene, $-(CH_2)_4C$ or mono-, di- or tri-$C_1 - C_5$ alkyleneamine group, Y is a $C_1 - C_8$ alkylene, $C_4 - C_{18}$ alkylidene group or a sulfur atom, $R_1$ and $R_2$ are each a hydrogen atom or $C_1 - C_4$ alkyl group and $R_1$ and $R_2$ may be the same or different, $R_3$, $R_4$ and $R_5$ are each $C_1 - C_{18}$ alkyl group and $R_3$, $R_4$ and $R_5$ may be the same or different, n is an integer of 1 to 4 and m is an integer of 1 to 5 and said hindered amine antioxidant being a compound of the formula, wherein $R_6$ is a $C_1 - C_{18}$ alkyl, aryl, aralkyl or $C_6 - C_{12}$ cycloalkyl group, $R_7$, $R_8$, $R_9$ and $R_{10}$ are independently a hydrogen atom or a $C_1 - C_8$ alkyl or alkoxy group, $R_{11}$, $R_{12}$ $R_{13}$, $R_{14}$, $R_{15}$, $R_{16}$, $R_{17}$ and $R_{18}$ are independently a hydrogen atom or a $C_1 - C_{18}$ alkyl group, and n' is 1 and wherein the weight ratio of the ultraviolet absorber (A-1) to the antioxidant is 1:9 to 9:1.

* * * * *